US009062321B2

(12) United States Patent
Mor et al.

(10) Patent No.: US 9,062,321 B2
(45) Date of Patent: Jun. 23, 2015

(54) CODON-OPTIMIZED POLYNUCLEOTIDES ENCODING HUMAN BUTYRYLCHOLINESTERASE AND PLANT EXPRESSION SYSTEMS THEROF

(75) Inventors: Tsafrir S. Mor, Tempe, AZ (US); Brian C. Geyer, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 746 days.

(21) Appl. No.: 11/792,985

(22) PCT Filed: Dec. 1, 2005

(86) PCT No.: PCT/US2005/043929

§ 371 (c)(1), (2), (4) Date: May 23, 2007

(87) PCT Pub. No.: WO2007/040568

PCT Pub. Date: Apr. 12, 2007

(65) Prior Publication Data

US 2009/0274679 A1 Nov. 5, 2009

Related U.S. Application Data

(60) Provisional application No. 60/632,551, filed on Dec. 1, 2004.

(51) Int. Cl.

*C12N 15/82* (2006.01)
*A01H 5/00* (2006.01)

(52) U.S. Cl.

CPC .................................. *C12N 15/8257* (2013.01)

(58) Field of Classification Search

None

See application file for complete search history.

(56) References Cited

U.S. PATENT DOCUMENTS

| | | | | |
|---|---|---|---|---|
| 5,248,604 | A | 9/1993 | Fischer | |
| 5,304,712 | A * | 4/1994 | Harper, II | 800/320.1 |
| 5,595,903 | A | 1/1997 | Soreq et al. | |
| 6,770,799 | B2 | 8/2004 | Mor et al. | |
| 8,030,540 | B2 * | 10/2011 | Guan et al. | 800/281 |
| 8,119,784 | B2 * | 2/2012 | Zhu et al. | 536/23.2 |
| 8,153,859 | B2 * | 4/2012 | Meyer et al. | 800/278 |
| 8,237,014 | B2 * | 8/2012 | Blaylock et al. | 800/278 |
| 8,399,736 | B2 * | 3/2013 | Meyer et al. | 800/278 |
| 8,535,930 | B2 * | 9/2013 | Williamson et al. | 435/252.3 |
| 8,586,832 | B2 * | 11/2013 | Abad et al. | 800/302 |
| 8,592,651 | B2 * | 11/2013 | Li et al. | 800/301 |
| 2004/0148657 | A1 | 7/2004 | Mor et al. | |
| 2007/0111279 | A1 | 5/2007 | Rosenberg | 435/69.1 |
| 2007/0134205 | A1 | 6/2007 | Rosenberg | 424/93.2 |

FOREIGN PATENT DOCUMENTS

WO WO 2005/000195 1/2005

OTHER PUBLICATIONS

Wei et al. Purification of genetically engineered human butyrylcholinesterase and detoxification of succinylcholine in vitro. (2002) Chinese Journal of Pharmacology and Toxicology; vol. 16; pp. 454-458.*

Giddings, G. Transgenic plants as protein factories. (2001) Current Opinion in Biotechnology; vol. 12; pp. 450-454.*

Platteborze et al. Expression of biologically active human butyrylcholinesterase in the cabbage looper (*Trichoplusia ni*). (2000) Biotechnol. Appl. Biochem.; vol. 31; pp. 225-229.*

Arpagus et al. (2010) Swiss-Prot P06276.1; pp. 1-13.*

Streatfield et al. Corn as a production system for human and animal vaccines. (2003) Vaccine; vol. 21, pp. 812-815.*

Gomord et al. Posttranslational modification of therapeutic proteins in plants. (2004) Current Opinion in Plant Biology; vol. 7; pp. 171-181.*

Sun et al. Re-engineering butyrylcholinesterase as a cocaine hydrolase. (2002) Molecular Pharmacology; vol. 62; pp. 220-222.*

Duysen, E., et al.; "Wild-type and A328W mutant human butyrylcholinesterase tetramers expressed in chinese hamster ovary cells have a 16-hour half-life in the circulation and protect mice from cocain toxicity;" article; J Pharmacol & Exp Therap; Jan. 29, 2002; V 302, N 2; pp. 751-758.

Giddings, G.; Transgenic plants as protein factories; article; Current Op in Biotech; 2001; V 12; pp. 450-454.

Masson, P., et al.; "Expression and refolding of functional human butrylcholinesterase from *E. coli*;" chapter; Multidisciplinary Approaches to Cholinesterase Functions, eds A. Shafferman, B. Velan, Plenum Press, NY, NY, 1992, pp. 49-52.

Platteborze, P., et al.; "Expression of biologically active human butyrylcholinesterase in the cabbage looper (*Trichoplusia ni*)," article; Biotech Appl Biochem; 2000; V 32; pp. 225-229.

Wei, W., et al.; "Purification of genetically engineered human butyrylcholinesterase and detoxification of succinylcholine in vitro," article; Chinese J Pharmcol Toxicol; Dec. 2002; V16(6); pp. 454-458.

Ben Aziz-Aloya, R., et al., "Expression of a human acetylcholinesterase promoter-reporter construct in developing neuromuscular junctions of *Xenopus* embroyos", article, Proc Natl Acad Sci USA 90: pp. 2471-2475, Mar. 1993.

Fletcher, S., et al., "Tissue distribution of cholinesterases and anticholinesterases in native and transgenic tomato plants," article, Plant Mol Biol, May 2004; 55(1):33-43.

Mor, T., et al., "Expression of recombinant human acetylcholinesterase in transgenic tomato plants," article, Biotech Bioeng, Nov. 5, 2001; 75(3):259-66.

(Continued)

*Primary Examiner* — Cathy Kingdon Worley

(74) *Attorney, Agent, or Firm* — Norton Rose Fulbright US LLP

(57) ABSTRACT

The present invention concerns the production of human butyrylcholinesterase (BuChE) in plants expressing a codon-optimized polynucleotides for the production thereof and use of the derived BuChE as effective counter measures against toxic agents such as pesticides, toxins, certain drugs and non-conventional warfare agents, as well as treatments for diseases and conditions associated with depressed cholinesterase levels.

9 Claims, 5 Drawing Sheets

(56) References Cited

OTHER PUBLICATIONS

Ordentlich, A., et al., "Dissection of the human acetylcholinesterase active center determinants of substrate specificity," article, J Bio Chem, V 268, N 23, Aug. 15, 1993, pp. 17083-17095.

Soreq, H., et al., "Molecular cloning and construction of the coding region for human acetylcholinesterase reveals a G+C-rich attenuating structure", article, Proc Nat Acad Sci USA 87: pp. 9688-9692, Dec. 1990.

Sun, H., et al., "Cocaine metabolism accelerated by re-engineered human butyrylcholinesterase," article, J Pharmacol Exp Ther, Feb. 5, 2002, 302: 710-16.

Sun, H., et al., "Re-engineering butyrylcholinesterase as a cocaine hydrolase," article, Mol Charmacol, Feb. 26, 2002, 62:220-24.

* cited by examiner

FIG. 5

CODON-OPTIMIZED POLYNUCLEOTIDES ENCODING HUMAN BUTYRYLCHOLINESTERASE AND PLANT EXPRESSION SYSTEMS THEROF

CLAIM TO FOREIGN PRIORITY

This Application claims the benefit of priority of PCT Application Serial No. PCT/US2005/043929 filed Dec. 1, 2005.

CLAIM TO DOMESTIC PRIORITY

This Application claims the benefit of priority of U.S. Application Ser. No. 60/632,551 filed Dec. 1, 2004.

FEDERAL FUNDING STATEMENT

This invention was made with United States government support awarded by the following agency: DARPA N66001-01-C-8015. The United States of America has certain rights in this invention.

FIELD OF THE INVENTION

The present invention relates to the field of transgenic plants and, more specifically, the invention relates to the production of human butyrylcholinesterase (BuChE) in transgenic plants and use of the derived BuChE as effective countermeasures against toxic agents such as pesticides, toxins, certain drugs and non-conventional warfare agents, as well as treatments for diseases and conditions associated with depressed cholinesterase levels.

BACKGROUND OF THE INVENTION

Acetylcholinesterase (ACHE) and butyrylcholinesterase (BuChE) are hydrolyzing enzymes present in various human or animal tissues, including plasma, muscles and brain. AChE functions primarily to hydrolyze acetylcholine and is essential to proper neuronal and neuromuscular activity (e.g., in regulation of chemical synapses between neurons and in neuromuscular junctions). BuChE is a serum cholinesterase with a broad hydrolytic spectrum that provides protection against a variety of AChE inhibitors. A similar end may be achieved by a variant of AChE found on the membranes of erythrocytes. Both enzymes are believed to serve as circulating scavengers for anti-AChE agents in protection of the vital synaptic ACHE. Therefore, administration of cholinesterases has the ability to boost natural human ability to counteract the toxic effects of anti-cholinergic agents.

While AChE and BuChE are both cholinesterases that may be used to counteract the toxic effects of anti-cholinergics and other toxic agents, their biochemical properties are distinct. Further, the amino acid sequences of the two enzymes are only 50% identical, with critical differences in several key positions.

For example, AChE displays nearly 100-fold selectivity toward acetylcholine over the longer chain butyrylcholine. Most of this increase is due to a 50-fold increase of $K_{cat}$ (a measure of catalytic efficiency) and only 2-fold increase in the $K_m$ (a measure of substrate affinity). Conversely, BuChE has no significant substrate selectivity with both $K_m$ and $K_{cat}$ nearly the same for both substrates. In addition AChE is inhibited by substrate inhibition above 2 mM, while BuChE is activated by substrate concentrations in the range of 20-40 mM. In addition, BuChE is reactive against a variety of substrates, for example, cocaine, for which ACHE is practically refractory.

Various compounds are well known to inhibit the hydrolyzing activity of human cholinesterases. Exposure to such anti-cholinesterase agents leads to over-stimulation of cholinergic pathways, causing muscular tetany, autonomous dysfunction and, potentially, death. While some naturally-occurring cholinesterase inhibitors are very potent, human exposure to them is rare. However, man-made anti-cholinesterase compounds, especially organophosphates (OPs), are widely used as pesticides and pose a substantial occupational and environmental risk. Even more ominous is the fear of deliberate use of OPs as chemical warfare agents against individuals or populations.

Availability of an agent specific cholinesterase provides a more effective treatment of anti-cholinergic response because AChE and BuChE differ in their sensitivity to many inhibitors. For example, BuChE is much more sensitive to the organophosphate tetraisopropyl pyrophosphoramide (Iso-OMPA), while ACHE is generally much more sensitive to cholinesterase inhibitors such as Diisopropylfluoro-phosphate (DFP) and 1,5-bis(4-allyldimethylammoniumphenyl) pentan-3-one dibromide, (BW284c51). The $K_i$, (or measure of inhibitor efficiency) against BW284c51 for ACHE is 10 nM (nano moles/liter), and for BuChE is 14,000 nM (or 14 µM), which represents a 1400-fold difference in sensitivity of BuChE compared to AChE.

Current medical interventions, in the case of acute exposure to anti-cholinesterase agents, include use of the muscarinic receptor antagonist, atropine, and oximes to reactivate the OP-modified cholinesterase. The reversible carbamate, pyridostigmine bromide, is also used as a prophylactic. However, these conventional treatments have limited effectiveness and have serious short- and long-term side effects. In fact, the routine treatments, while successfully decreasing anti-cholinesterase-induced lethality, rarely alleviate post-exposure delayed toxicity, which may result in significant performance deficits and even permanent brain damage.

A different approach in treatment and prevention of anti-cholinesterase toxicity seeks to mimic one of the physiological lines of defense against such agents present in mammals. The efficacy of this treatment to protect against a challenge of OPs was tested in a variety of animal models, such as mice, rats, guinea pigs, and primates, and was found to be comparable to or better than the currently-used drug regimens in preventing OP-induced mortality without any detrimental side-effects.

Naturally-occurring cholinesterases in human plasma are known to be important in metabolizing systemic toxins and have been tested in a range of animal models, particularly in cocaine detoxification. Naturally-occurring levels in the human body are limited in therapeutic applications, because these levels are so low. Genetic modification of natural cholinesterases to improve catalytic efficiency has shown promise as treatment for drug detoxification. More specifically, recombinant BuChE, produced using bacterial transformation, and then transfected into human kidney cells, was shown to increase cocaine hydrolysis. Though cholinesterases are known to be effective as anti-neurotoxins, the largest limitation in use of ChEs is the cost-effective production of sufficient quantities.

Despite the promise of cholinesterases as an effective treatment against nerve-agent intoxication and other toxins, the practicality of this therapeutic approach depends on the availability of large amounts of these enzymes, which are required in stoichiometric rather than catalytic quantities. Currently, human-plasma derived BuChE has been identified by the US military as a first generation candidate to go into human clinical trials. However, a reliable, safe, non-supply-limited and inexpensive source of ChEs is still needed, because a stock pile of 1 kg of pure enzyme would require dedicating the whole annual US supply of outdated plasma to a purification effort at an enormous cost.

Genetically-engineered plants have recently been recognized as one of the most cost-effective means for the production of useful recombinant proteins and pharmaceuticals. Expressing human enzymes, and more particularly human acetylcholinesterase, in plants is known in the art; however, no system or method has yet been disclosed for optimizing human BuChE-enzyme expression in plants. Therefore, a need exists for a method of optimizing human gene expression of human BuChE in plants and, more specifically, for a method for increasing the levels of expression of human BuChE enzymes in plants by optimizing the expression constructs that encode the expression constructs for expression in plants.

DETAILED DESCRIPTION OF THE INVENTION

The present invention pertains to the field of transgenic plants. More particularly, the invention pertains to the production of human butyrylcholinesterase (BuChE) from transgenic plants for effective countermeasures against pesticides, toxins, drugs, and non-conventional warfare agents, as well as treatments for diseases and conditions associated with depressed cholinesterase levels. Plant-production of these enzymes offers high-quality, high-yield enzymes that are equivalent to enzymes derived from other sources. The plant-derived enzymes also have improved safety because there are significantly reduced concerns of human pathogen and prion contamination.

In addition, plant-derived enzymes have the potential for large-scale production in a short time frame and also provide production flexibility with low capital investment because large stockpiles of raw material (transgenic seeds) can be produced and stored in dispersal locations with purification initiated only when required. In addition, plant-derived enzymes provide significant savings on production costs, costs of raw materials, purification cost and regulatory costs when compared with other production systems. Overall, production of genetically-modified BuChE using plant expression hosts provides an alternative and potentially more effective method of counteracting the toxic effects of anti-cholinergic agents and other toxic agents.

In one embodiment, the invention relates to the optimization of DNA constructs encoding the human BuChE enzyme. In another embodiment, the invention relates to transgenic plants harboring these constructs and expressing these genes (in cells, organs, and seeds thereof). In a further embodiment, the invention relates to a method of purification of BuChE enzymes from plants. In an additional embodiment, the invention relates to use of the BuChE enzyme for the purpose of treating and preventing the harmful effects of toxic agent exposure in humans produced by nerve-agents, toxin, pesticides, certain drugs, and non-conventional warfare agents.

The technology of the invention involves engineering DNA constructs directing the recombinant expression of cholinesterases in transgenic plants, in either leaf or seeds. As disclosed herein in the following examples, transgenic plants were selected and grown under USDA-approved standard operating procedure (SOP) for genetic containment, and high-yield purification procedures for the plant-produced human protein variants were developed. It is envisioned the plants and methods disclosed herein would be used as an antidote for and prevention against toxic agents, including for anti-cholinergic response, by homeland security agencies, the military, life sciences and high technology companies, in hospitals and medical treatment facilities, and by public health agencies.

Specifically, cholinesterases can provide protection from the lethal and incapacitating effects of chemical warfare or pesticide nerve-agent intoxication. For example, cholinesterases can be used in actual or potential medical, security, or emergency situations including following prophylaxis in the case of anticipated exposure, for post-exposure treatment, as topical skin protectants, in personal or large filtering devices, such as gasmasks, and in decontamination of equipment and buildings. The protein products may further be used as a clinical treatment for cocaine overdose to aid in detoxification for overdose victims or cocaine users. BuChE may also be used as a component in a drug treatment plan to prevent future drug use, as patients with enhanced BuChE levels fail to experience a "high" from cocaine administration.

In addition, BuChE may also be used as a treatment or preventative in pesticide or chemical exposure. BuChE may also be used as a medical treatment for disorders or conditions associated with anti-cholinergic responses such as post-surgical apnea. Additionally, protein products from plants expressing BuChE sequences disclosed herein may also be used in the treatment of patients displaying prolonged neuro-muscular blockade following succinylcholine administration, including conditions which may occur as a result of a patient's genetic mutation in the BuChE sequence.

Traditionally, cholinesterases are classified as either acetylcholinesterase (EC 3.1.1.7, AChE) or as butyrylcholine hydrolases (EC 3.1.1.8, BuChE, formerly referred to as pseudo-acetylcholinesterase) on the basis of their substrate specificity. While BuChE can efficiently hydrolyze substrates with a longer acyl group, the catalytic efficiency of AChE is limited to acetylcholine and, to a lesser degree, propionylcholine. More recently inhibitors have been identified that can selectively inhibit the two types of cholinesterases. AChE and BuChE have been shown to have similar effects in binding to nerve agents, typically demonstrating binding at a 1:1 ratio. Thus, it is expected that both enzymes offer similar levels of protection against these agents.

However, the AChE and BuChE enzymes have very different catalytic properties, and pharmacokinetic results are predicted to be completely different, based on preliminary substrate sensitivity differences between the enzymes, as shown in Table 1 (adapted from Kaplan, et al. Biochemistry 40:7433-7445, 2001), comparing the substrate sensitivity of AChE and BuChE.

TABLE 1

| Enzyme | Substrate: | | | | | |
|---|---|---|---|---|---|---|
| | Acetylthiocholine | | | Butyrylthiocholine | | |
| | Km mM | Kcat ×10$^{-5}$ min$^{-1}$ | Kcat/Km ×10$^{-5}$ mM$^{-1}$min$^{-1}$ | Km mM | Kcat ×10$^{-5}$ min$^{-1}$ | Kcat/Km ×10$^{-5}$ mM$^{-1}$min$^{-1}$ |
| Aceylcholinesterase | 0.14 | 4.0 | 29 | 0.3 | 0.08 | 0.3 |
| normalized | 1.00 | 1.00 | 1.00 | 2.14 | 0.02 | 0.01 |
| Butyrylcholinesterase | 0.04 | 0.5 | 13 | 0.05 | 1.1 | 22 |
| normalized | 1.00 | 1.00 | 1.00 | 1.25 | 2.20 | 1.69 |

As described herein in various embodiments, the human enzyme BuChE, is produced in plants and administered as a pre-exposure prophylactic measure to block entry of toxic agents and/or prevent them from reaching their target tissues in the body or as a post-exposure treatment. Further, in alternate embodiments, the human BuChE produced in plants is applied to surfaces that have been exposed to a toxic agent. In one embodiment, the surface to which the human BuChE is applied is human skin that has been exposed to a toxic agent. Application of plant derived human BuChE to exposed surfaces reduces further human exposure, both internal and external, to the toxic agent and the harmful effects associated with the agent.

More specifically, butyrylcholinesterase disclosed herein is used as a "passive line of defense" to supplement circulating cholinesterases in individuals exposed to chemicals, in order to prevent toxic agents from reaching their target tissues. These uses include, but are not limited to the following: as a pre-treatment for individuals that may be exposed to warfare agents, as a pre-treatment for individuals with the potential to be exposed to toxic chemicals or pesticides, as a pre-treatment in patients known to have BuChE mutations in preparation for medical treatments, and as a pre-treatment to prevent drug users from feeling the effects of drugs.

As used herein, this is understood that "plant" may refer generally to a whole plant, or any portion of a plant, including cells, tissues, tissue cultures, seeds, roots, leaves, pollen, and other plant structural components. Numerous types of plants, including both monocotyledonous and dicotyledonous plants, may be modified or engineered within the scope of the plants and method described herein. Non-limiting examples of families of plants that may be used include Solanaceae, Fabaceae (Leguminosae), Chenopodiacae, Brassicaceae, and Graminea. Specific genre of plants that may be used include, but are not limited to, *Arabadopsis* sp., *Brassica* sp., *Nicotiana* sp., *Lycopersicon* sp., *Solanum* sp., *Medicago* sp., *Glycine* sp., *Chenopodium* sp., and *Spinacia* sp., *Zea* sp., *Oryza* sp., *Hordeum* sp. However, it is recognized that these are given as non-limiting examples only.

Figure 4:
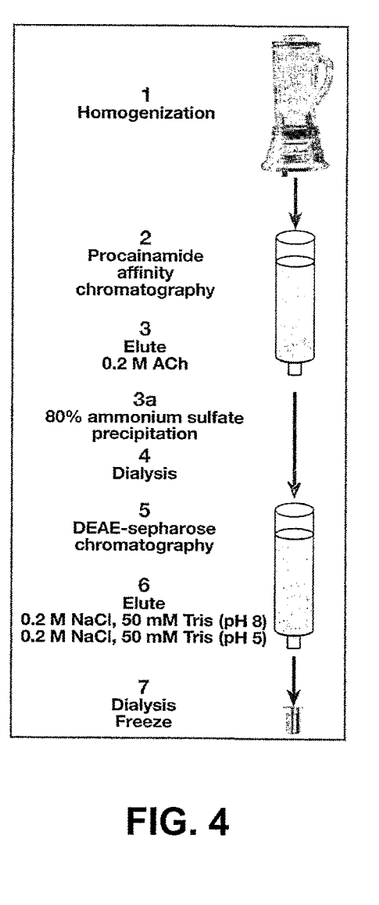
FIG. 4 is a schematic drawing of a large-scale purification procedure for the purification of BuChE.
Figure 5:
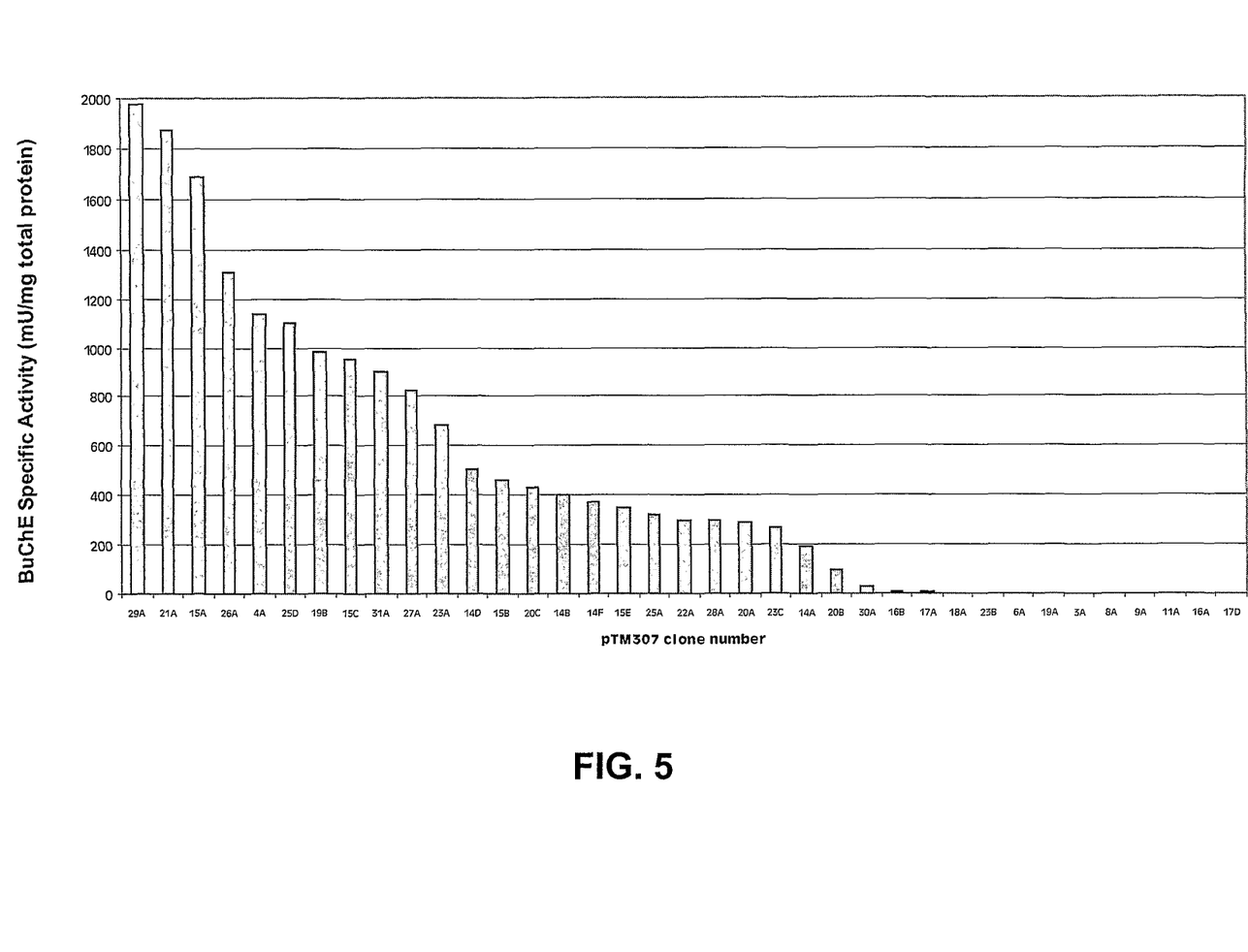
FIG. 5 is a graph illustrating results of the specific activity of plants optimized with pTM307.

The use of BuChE as disclosed herein may further include additional purification steps in the processing of the plants or methods disclosed herein in order to improve product yield and purity. In one embodiment, the purification step may be performed at the industrial scale level. For example, large-scale purification of plant derived BuChE for purification of cholinesterases from serum may include an affinity purification step using procainamide-agarose, elution with free procainamide and extensive dialysis, followed by DEAE-sepharose anion exchange chromatography to achieve additional purification, as shown in FIG. 4.

Industrial scale equipment and techniques, particularly continuous-flow centrifugation, are optimized to clarify the plant extract at sufficient rates to overcome the problem of polyphenol oxidase-induced browning (which may be present where purification is done at slower rates). Other variations on this method of purification include variation in resins, and use of various concentrations of acetylcholine to elute procainamide-bound cholinesterases, and anion-exchange steps into order to improve yield.

In another embodiment, as disclosed in Example 5 below, the optional purification step may include processing the plant material on a smaller scale, such as in 500 gram batches. A smaller scale purification process may be more time-consuming or labor-intesive approach; however, for example, where industrial equipment is unavailable or large quantities are not required, this method has been shown useful for the propessing of 2 kg/day plants.

Example 1

Optimization of Human BuChE for Plant Expression (pTM307) Removal of "Unpreferred" Codons One strategy of optimizing human BuChE for plant production is performed by genetically modifying human BuChE to remove all unpreferred codons. As shown in Table 2 below, a codon adaptiveness index (CAI) is first constructed to determine the relative abundance of codons from highly-expressed proteins in a related plant species, *Arabidopsis thaliana*.

The CAI is a mathematical expression of the use of each codon relative to the use or the other codons which code for the same amino acid. A threshold of 0.8 is set, whereby codons with a CAI below this value are deemed "unpreferred". Under this strategy, these unpreferred codons are replaced with more preferred codons. A "good" codon is defined as the codon with the highest CAI. A "good" codon is defined as the most preferred codon, which is most abundant in the sequence, and therefore is most closely associated with BuChE expression. A bad codon is a codon with a CAI of 0.8 or less.

Figure 1:
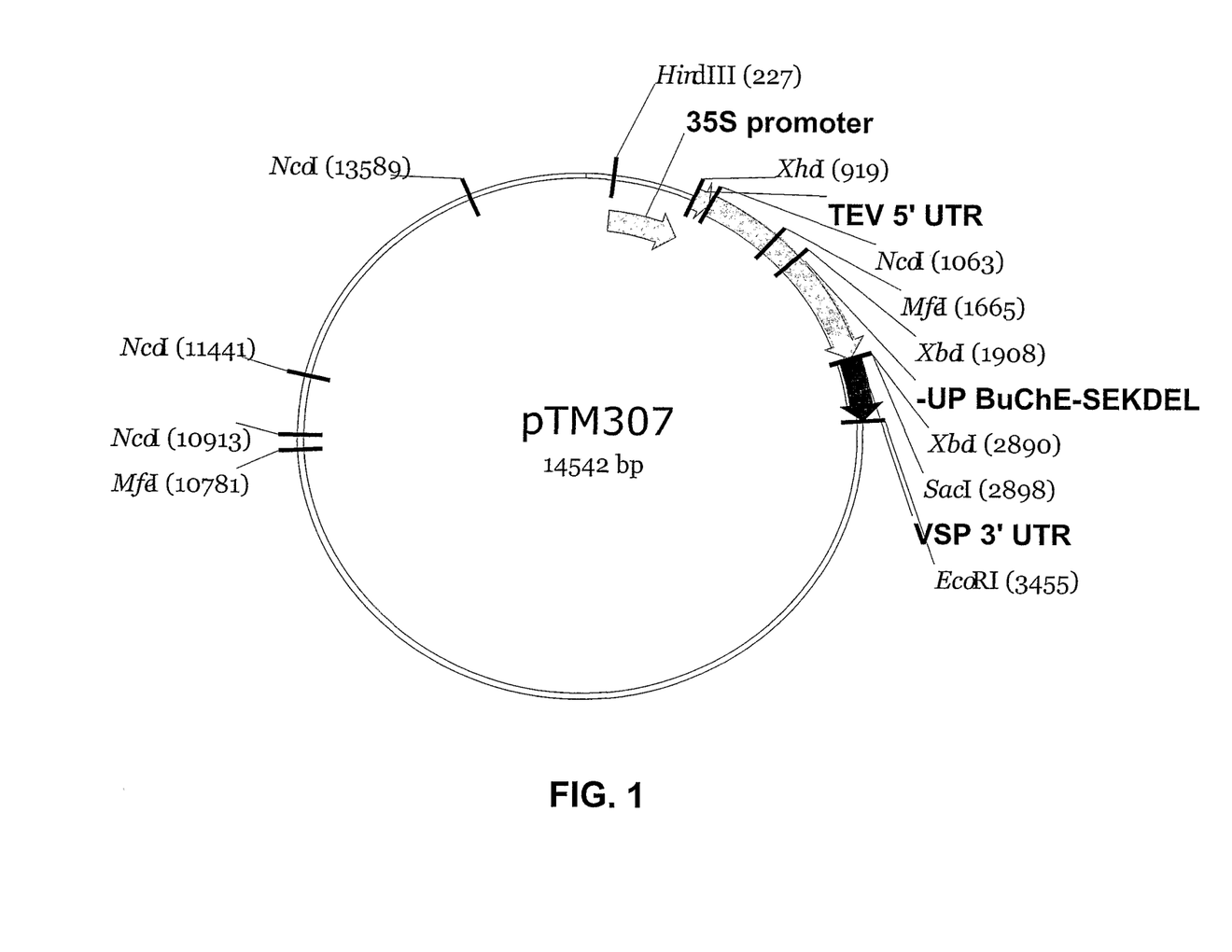
FIG. 1 is a graphic illustration of the construct pTM307, shown as a human butyrylcholinesterase plasmid map.
Figure 2:
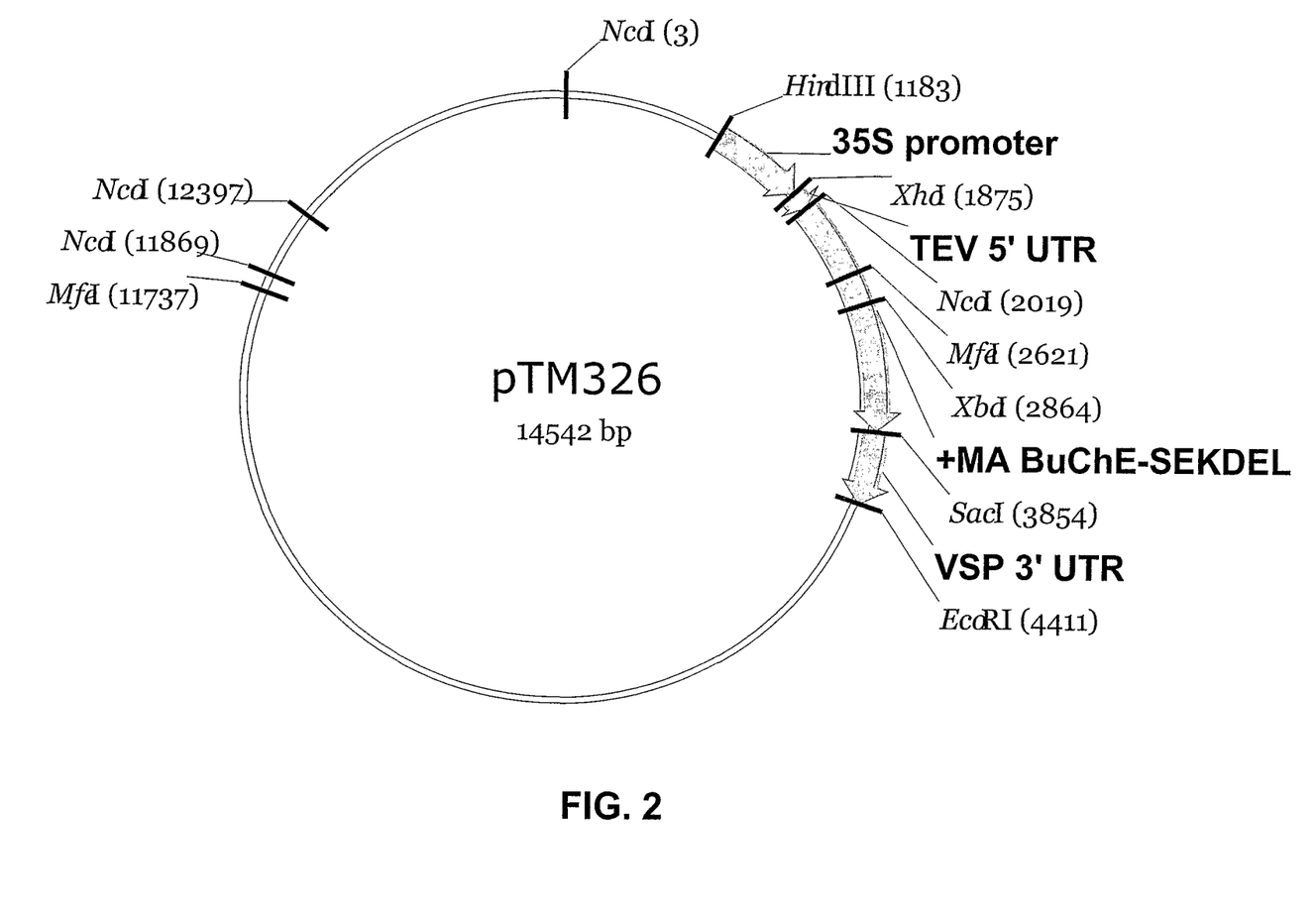
FIG. 2 is a graphic illustration of the construct pTM326, shown as a human butyrylcholinesterase plasmid map.
Figure 3:
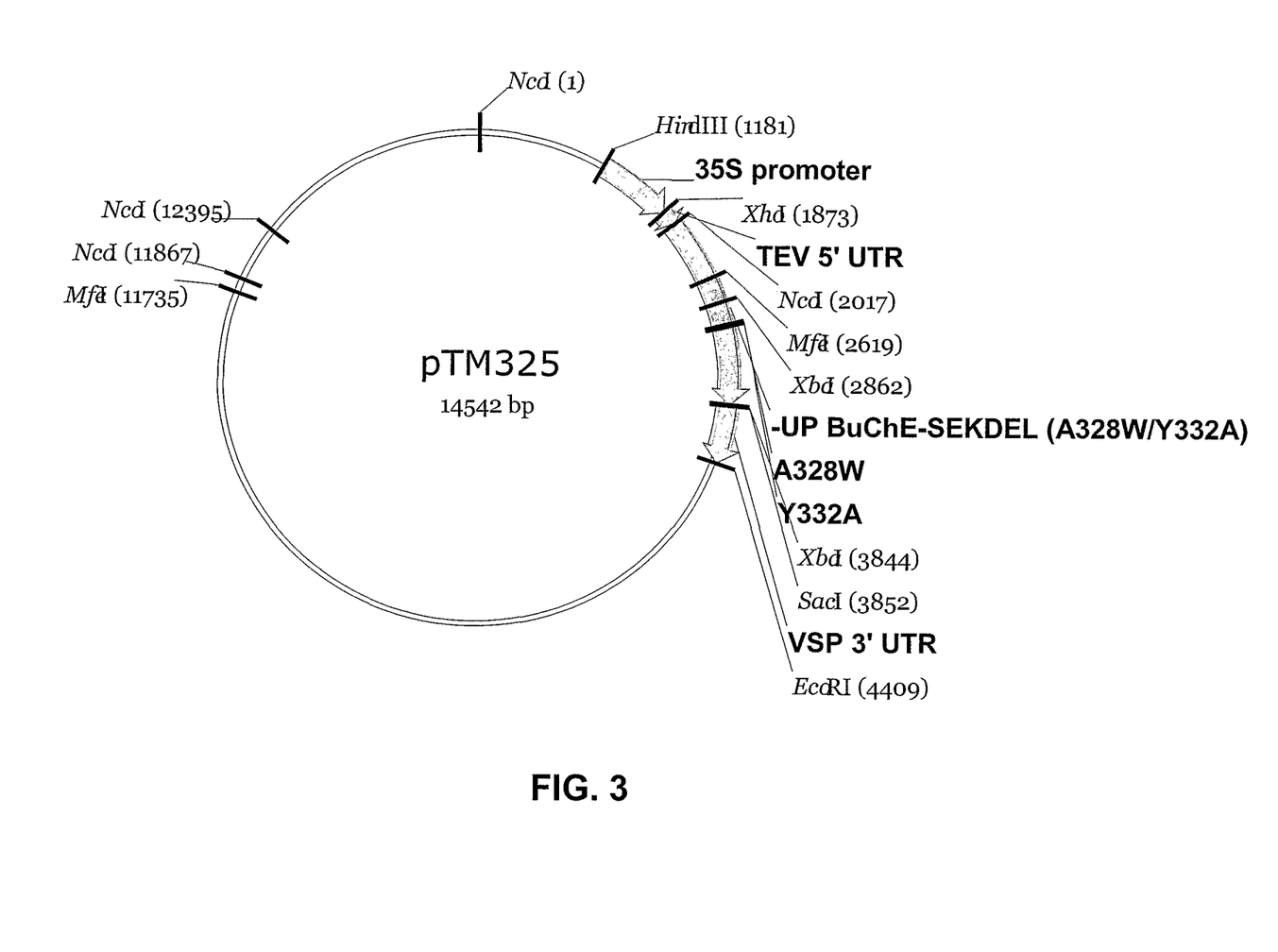
FIG. 3 is a graphic illustration of the construct pTM325, shown as a human butyrylcholinesterase plasmid map.

Following the optimization, as shown in FIG. 1, CG and CNG potential methylation sites are removed, as well as all potential deleterious sequences (Cryptic introns, splice sites, etc.). Optimization also includes the addition of a c-terminal SEKDEL (Ser-Glu-Lys-Asp-Glu-Leu) (SEQ ID NO:4). This construct is designated as pTM307, as shown in FIG. 1. Table 2, illustrates pTM307 human butyrylcholinesterase sequence codon optimization index and deletions, performed by removing all unpreferred codons and replacing them with a more preferred codon, as well as the addition of a c-terminal SEKDEL. The modified hBuChE nucleotide sequence, which is inserted into the plasmid pTM307, is further represented as SEQ ID 1.

TABLE 2

|  | human | −up |
|---|---|---|
| Good | 39.57% | 57.47% |
|  | 22.82% | 34.98% |
| Bad | 37.74% | 7.55% |
| G + C % | 39.74% | 44.94% |
| CG | 19 | 2 |
| CNG | 87 | 63 |
| Del. Seq. | 30 | 0 |

Table 2 illustrates pTM307 human butyrylcholinesterase sequence codon optimization index, performed by removing all unpreferred codons and replacing them with a more preferred codon, as well as the addition of a c-terminal SEKDEL. The modified hBuChE nucleotide sequence, which is inserted into the plasmid pTM307, is represented as SEQ ID 1.

Example 2

Optimization of Human BuChE for Plant Expression (pTM326) Replacement with "Most Preferred" Codons Another strategy of optimizing human BuChE for plant production is performed by genetically modifying human BuChE such that existing codons are removed and replaced with "most preferred" codons. Analysis of all existing *Nicotiana benthamiana* sequences deposited with GENBANK was conducted using the software available at the Kazusa DNA Research Institute's codon usage database. Available at http://www.kazusa.or.jp/codon/. As shown in Table 3, below, the most preferred codon for each amino acid is identified and the BuChE gene is optimized such that all amino acids are expressed by this codon. A "good" codon is defined as the most preferred codon, while a "bad" codon is defined as 50% less abundant than the most abundant codon.

Then, as shown in Table 3, below, the human butyrylcholinesterase sequence is codon optimized by genetically modifying human BuChE to remove all but the most abundant codon (as determined using GENBANK) and replacing the removed codons with additional copies of the most abundant "preferred" codon. A c-terminal SEKDEL is also added. Following the optimization, CG and CNG potential methylation sites are removed, as well as all potential deleterious sequences (Cryptic introns, splice sites, etc.). This construct is designated pTM326, as shown in FIG. 2.

TABLE 3

| | Human | +mp |
|---|---|---|
| Good | 51.89% | 92.61% |
| | 33.00% | 6.73% |
| Bad | 15.11% | 0.66% |
| G + C % | 39.74% | 34.37% |
| CG | 19 | 2 |
| CNG | 87 | 55 |
| Del. Seq. | 30 | 0 |

Table 3 illustrates pTM326 human butyrylcholinesterase sequence codon optimization index and deletions, performed by genetically modifying human BuChE to remove all but the most abundant codon from GENBANK and replacing the removed codons with additional copies of the abundant "preferred" codons. The modified hBuChE nucleotide sequence, which is inserted into the plasmid pTM326, is further represented as SEQ ID 2.

Example 3

Optimization of Human BuChE for Plant Expression (pTM325) Replacement with "Most Preferred" Codons and Targeted Mutations As a modification of the strategy shown in Example 2, specific amino acid mutations may also be added after naturally occurring codons are replaced with "most preferred" codons. As in Example 2, analysis of all existing *Nicotiana benthamiana* sequences deposited with GENBANK was conducted using the software available at the Kazusa DNA Research Institute's codon usage database. Available at http://www.kazusa.or.jp/codon/. As shown in Table 3, above, the most preferred codon for each amino acid is identified and the BuChE gene is optimized such that all amino acids are expressed by this codon. A "good" codon is defined as the most preferred codon, which is most abundant in the sequence, and appears to be linked to optimized BuChE expression. A "bad" codon is defined as 50% less abundant than the most abundant codon.

Then, as shown in Example 2, the human butyrylcholinesterase sequence is codon optimized by genetically modifying human BuChE to remove all but the most abundant codon (as determined using GENBANK) and replacing the removed codons with additional copies of the most abundant "preferred" codon. A c-terminal SEKDEL is also added. This step is followed by making amino acid mutations at A328W and Y332A, which has been disclosed in the literature as a BuChE with enhanced activity as a cocaine hydrolase. Following the optimization, CG and CNG potential methylation sites are removed, as well as all potential deleterious sequences (Cryptic introns, splice sites, etc.). As shown in FIG. 3, this construct is designated pTM325. The modified hBuChE nucleotide sequence, which is inserted into the plasmid pTM325, is further represented as SEQ ID 3.

Example 4

Comparison of pTM307 and pTM326

Homology between the constructs pTM307 and pTM326 is determined using Vector NTI software suite (Invitrogen, Carlsbad, Calif.) and then using the multiple sequence alignment application Align X (Invitrogen, Carlsbad, Calif.) for comparisons. Sequences are entered into Vector NTI software suite and sequences are aligned according to the following parameters: K-tuple size—1; Number of best diagonals—5; Window size—5; Gap penalty—3; Gap opening penalty—10; Gap extension penalty—0.1. Results of the analysis between pTM307 and pTM326 reveals 82.2% homology at the DNA level, and, as expected, 100% homology at the protein level.

Example 5

Purification

The presence of polyphenoloxidases in the plant extracts is a major interfering factor in the purification. It is envisioned that additional techniques for purification are applicable, as disclosed herein and as are known in the art. For example, the following additional techniques may be used for purification: substances that eliminate by adsorption the substrate polyphenols (e.g., polyvinylpyrrlidone, PVPP) and reductants that inhibit the enzymes (e.g., dithiotreitol and ascorbic acid). In order to facilitate the purification of BuChE from plant extracts, additional purification schemes that involve engineering a tag to the recombinant enzyme by creating translational fusions are also envisioned.

One specific example of purification, using a 500 gram batch, is illustrated as follows. Purification at 4° C. is performed according to the following steps. First, *Nicotiana benthamiana* leaves and stems (455 g) are homogenized in a blender (2×30 s) with 1.4 L phosphate buffered saline containing 4 mM DTT, 5 mM $MgCl_2$ and 10% (w/v) sucrose. Next, the pH is adjusted to 8.0 and the lysate is then filtered through double-thickness Miracloth (Calbiochem, Gibbstown, N.J.) and clarified by centrifugation at 8,200×g for 30 minutes. Then, 50% ammonium sulfate is added and the sample is stirred at 4 C for 1 hour, then centrifuged at 8,200×g for 30 minutes. Following this step, the supernatant is discarded and the pellet is re-suspended in 150 mL Buffered Saline (PBS). This is then clarified by centrifugation at 36,000×g for 30 minutes.

Then, the supernatant is loaded onto an Econo-Column (Bio-Rad, Hercules, Calif.) containing 100 mL procainamide-agarose (Sigma, St. Louis, Mo.). Following this step, the column is washed with 1 L PBS and eluted with 200 ml PBS containing 0.2 M acetylcholine. Two to 25 batches produced daily are pooled and concentrated with 50% ammonium sulfate. The resulting pellet is re-suspended in 80 ml 20 mM $KP_i$ buffer (pH 8.0) with 20 mM NaCl, dialyzed extensively against the same buffer and loaded onto a column containing DEAE-sepharose (Amersham Biosciences, Piscataway, N.J.). Then, the column is washed with 50 ml 20 mM Tris, pH 8.0 and 100 mM NaCl and protein eluted with 50 ml 20 mM Tris, pH 8.0 and 200 mM sodium chloride (NaCl). Finally, the eluate is then concentrated on a Macrosep 10K concentrator (Pall, Ann Arbor, Mich.) to a final volume of 1 ml and desalted on the same concentrator with 3×10 volumes of water.

As shown in Example 6, the resulting sample is then subjected to cholinesterase assays using the standard Ellman method, and analyzed with a SpectraMax 340PC spectrophotometer (Molecular Devices, Sunnyvale, Calif.). Storage is at −80° C. until later use. This purification method is used to process about 2 kg/day of plants, without significant polyphenol oxidase-induced browning problems.

Example 6

Plant Screening

In order to demonstrate the cholinesterase activity in plants expressing optimized BuChE enzymes, approximately 40 *Nicotiana benthamiana* plants expressing the optimized BuChE pTM307 are screened using an Ellman assay. Leaf samples taken from plants are homogenized in ice-cold extraction buffer (100 mM NaCl, 25 mM Tris, 0.1 mM EDTA, 10 μg/mL leupeptin (Sigma, St. Louis, Mo.), pH 7.4, 3 mL per 1 g tissue) using ceramic beads in a bead-beater (Fast-Prep machine, Bio 101, Savant, Holbrook, N.Y.).

Cleared supernatants are collected after centrifugation (microfuge, top speed for 10 minutes). Scaled-down microtiter plate Ellman assays are done essentially as described before. Cleared extracts (20 μL) are incubated for 30 minutes at room temperature with 80 μL assay buffer (0.1M phosphate buffer, pH 7.4) with or without $2 \cdot 10^{-5}$ M tetraisopropyl pyrophosphoramide (Iso-OMPA) (Sigma, St. Louis, Mo.), a specific inhibitor of mammalian BuChE.

At the end of the 30 minute incubation period 100 μL of 1 mM 5-5'-dithio-bis(2-nitrobenzoate) (Ellman's reagent, Sigma, St. Louis, Mo.) and 2 mM butyrylthiocholine (Sigma, St. Louis, Mo.) in assay buffer are added. Hydrolysis is monitored by measuring optical density at 405 nm for 30 minutes using a microtiter plate spectrophotometer (Molecular Devices, Sunnyvale, Calif.), plotted against time, and initial rates are calculated from the slope of the linear portion of the graph. Net hydrolysis rates are calculated by subtracting the rates measured in the presence of tetraisopropyl pyrophosphoramide (Iso-OMPA), from those obtained in its absence. Data are presented on the basis of total soluble protein determined by a modified Bradford assay as previously described in the literature. To determine the $K_m$, the concentration of the BuChE substrate in the Ellman's reagent is varied in the range of 0.05-50 mM. Data are subjected to Lineweaver-Burk analysis to obtain the $K_m$ value.

Inhibition curves are obtained by performing the Ellman assay with 1 mM BuChE in the presence of the indicated concentrations of diethyl p-nitrophenyl phosphate (paraoxon, Riedl-de. Haën), neostigmine (Sigma, St. Louis, Mo.) or Iso-OMPA (Sigma, St. Louis, Mo.). To determine kinetics, assays are performed in the presence of 1.0, 0.33 and 0.25 mM BuChE and the inhibitor at $10^{-4}$-$10^{-10}$ M. Results are then analyzed according to Ordentlich, et al., 268 *Journal of Biological Chemistry* 17083 (1993).

As shown in Table 4 and illustrated graphically in FIG. 5, individual plants expressed the following specific activity, as follows:

TABLE 4

| Clone Number | Specific Activity (nmol/min/mg) |
|---|---|
| 29A | 1980 |
| 21A | 1875 |
| 15A | 1686 |
| 26A | 1307 |
| 4A | 1139 |
| 25D | 1097 |
| 19B | 983 |
| 15C | 953 |
| 31A | 897 |
| 27A | 822 |
| 23A | 685 |
| 14D | 502 |
| 15B | 458 |
| 20C | 429 |
| 14B | 405 |
| 14F | 374 |
| 15E | 349 |
| 25A | 319 |
| 22A | 298 |
| 28A | 296 |
| 20A | 287 |
| 23C | 264 |
| 14A | 196 |
| 20B | 99 |
| 30A | 28 |
| 16B | 6 |
| 17A | 4 |
| 18A | 2 |
| 23B | 2 |
| 6A | 1 |
| 19A | 1 |
| 3A | 0 |
| 8A | 0 |
| 9A | 0 |
| 11A | 0 |
| 16A | 0 |
| 17D | 0 |

Example 7

Transformation of Plants with the New Vectors

In plants, antibiotic resistant-calluses from plants transformed with the BuChE nucleotide sequences in the plasmids represented as pTM307, pTM325, and pTM326 and are screened by PCR for the presence of transgenes. Ten clones are selected to be regenerated to seed to test for expression levels. In *Nicotiana benthamiana*, two top transgenic lines (T1 plants) expressing BuChE as well as wild-type propagated from seeds are selected on restrictive medium under tissue culture conditions, re-screened to ensure expression, and transferred to a greenhouse for further growth. Based on previous results with transgenic cholinesterase producing plants, it is expected that results for transformation of plants with new vectors will show a drop in recombinant product expression levels upon transfer to soil, but this will be more than offset by the increase in biomass.

Example 8

Large Scale Purification of Plant Derived Cholinesterase

BuChE-expressing plants are transformed with the pTM307, pTM325, and pTM326 constructs are purified with an anion-exchange step (FIG. 4), which is predicted to result in substantially more pure preparations of BuChE. It is also predicted that the average specific activity will be much greater, particularly where the adsorption of BuChE into DEAE-sepharose is controlled for, in order to minimize the amount of activity that is lost during the ion exchange step. Optimized techniques will also prevent insufficient dialysis associated with large eluate volumes, by introducing an ammonium sulfate precipitation step following the affinity purification step and prior to the dialysis (FIG. 4, step 3a).

Example 9

In-Vivo Testing, Pharmacokinetics of Plant-Derived BuChE

The amount of a chemical that is lethal to one-half (50%) of experimental animals fed the material is referred to as its acute lethal dose fifty, or LD50. Paraoxon LD50 is first determined in order to compensate for the uniqueness of every strain of mice. Paraoxon is administered by intraperitoneal (i.p) injection to 24 mice, delivered in 5 consecutive injections at 10 minute intervals. Mice are followed by observation, looking for the percent of survival and clinical signs, including the time from paraoxon challenge until animals die. Moribund animals are terminated by $CO_2$ asphyxiation.

Endogenous blood level of BuChE is determined for each mouse prior to the administration of the plant-derived enzyme. The BuChE for each construct (pTM307, pTM325, and pTM326) is expressed in plants, and is administered to groups of experimental animals. A commercially available preparation of BuChE is also administered to a group of experimental animals. Enzyme is delivered intravenously (tail vein) in approximately 10 µl of saline to 6 mice. Residual levels of activity in blood samples are assayed. Five to ten µl samples are drawn (retro-orbital vein, or by tail clipping) at 2, 30, 60, 90 minutes, and 2, 3, 4, 5, 6, 12 and 24 hour post-administration. Mice are terminated by exsanguination. BuChE exhibits completely different pharmacokinetic characteristics from AChE.

Example 10

Challenge/Protection Experiment Using Plant-Derived BuChE

Plant-derived BuChE enzyme for each construct (pTM307, pTM325, and pTM326) along with a commercially available preparations of BuChE are administered at the indicated amounts (see Example 10) intravenously (in approximately 10 µl of saline via tail vein) in 78 mice. Two hours after BuChE administration mice are challenged with paraoxon by i.p. injection in 2 doses –1×LDso or 2×LD50. The exact dose is determined in Example 10, as described above. Each paraoxon dose is delivered in 5 consecutive injections at 10 minute intervals. Mice are followed by observation, looking for the percent of survival and clinical signs, including the time from paraoxon challenge until the animals die.

Moribund animals are terminated by exsanguination. Blood level of BuChE is determined for each mouse prior to the administration of the plant-derived enzyme. To challenge the animals, paraoxon is administered. Prior to the paraoxon administration, 5-10 µl blood samples are drawn (retro-orbital vein, or by tail clipping). Residual levels of activity in blood samples are assayed after the terminal bleed. Surviving animals are kept for 4 weeks post exposure. Blood samples (100 µl) are collected by tail vein clipping at 1, 7, 14, 21, 28 days post exposure to determine residual cholinesterase activity (whole blood) and anti-cholinesterase (human, plant-derived and mouse), antibodies (by ELISA). It is predicted that the protection levels of BuChE will be comparable to AChE.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of a preferred embodiment and best mode of the invention known to the applicant at this time of filing the application has been presented and is intended for the purposes of illustration and description. It is not intended to be exhaustive nor limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out the invention.

What is claimed is:

1. A *Nicotiana* plant, or a part thereof, derived from a *Nicotiana* plant cell comprising a polynucleotide that encodes a human butyrylcholinesterase, wherein the polynucleotide is further defined as having a sequence that has been optimized for expression in a *Nicotiana* plant cell relative to a native human butyrylcholinesterase encoding sequence and the *Nicotiana* plant cell expresses the human butyrylcholinesterase polypeptide encoded by the polynucleotide, where a codon adaptiveness index of the sequence is 0.8 and where the codon adaptiveness index is derived from codon usage for a dicot plant.

2. A seed derived from the plant of claim 1, wherein said seed comprises said polynucleotide.

3. Pollen derived from the plant of claim 1, wherein said pollen comprises said polynucleotide.

4. The *Nicotiana* plant of claim 1, wherein the polynucleotide that encodes the optimized human butyrylcholinesterase comprises a nucleic acid sequence selected from the group consisting of SEQ ID 1, SEQ ID 2 and SEQ ID 3.

5. A *Nicotiana* plant cell comprising a polynucleotide that encodes a human butyrylcholinesterase, wherein the polynucleotide is further defined as having a sequence that has been optimized for expression in a plant cell relative to a native human butyrylcholinesterase encoding sequence and the plant cell expresses the human butyrylcholinesterase polypeptide encoded by the polynucleotide, wherein the polynucleotide that encodes the optimized human butyrylcholinesterase comprises SEQ ID 1, SEQ ID 2, or SEQ ID 3.

6. The *Nicotiana* plant of claim 1, where the codon adaptiveness index was derived solely from the codon usage for highly expressed proteins in the dicot plant.

7. A *Nicotiana* plant cell comprising a polynucleotide that encodes a human butyrylcholinesterase, wherein the polynucleotide is further defined as having a sequence that has been optimized for expression in a *Nicotiana* plant cell relative to a native human butyrylcholinesterase encoding sequence, where a codon adaptiveness index of the nucleotide is 0.8 and where the codon adaptiveness index is derived from codon usage of a dicot plant.

8. The *Nicotiana* plant of claim 1, where the codon adaptiveness index was derived from codon usage for a *Nicotiana* plant.

9. The *Nicotiana* plant of claim 1, where the codon adaptiveness index was derived from codon usage for an *Arabidopsis* plant.

* * * * *

SEQUENCE LISTING

<160> NUMBER OF SEQ ID NOS: 4

<210> SEQ ID NO 1
<211> LENGTH: 1827
<212> TYPE: DNA
<213> ORGANISM: Artificial Sequence
<220> FEATURE:
<223> OTHER INFORMATION: Synthetic Primer

<400> SEQUENCE: 1

| | | | | | |
|---|---|---|---|---|---|
| atgggacaca | gcaaggttac | catcatttgc | atcaggttcc | tcttttggtt | cctcctcctc | 60 |
| tgcatgctta | ttggtaagag | ccacactgag | gatgacatca | tcattgccac | caagaatggt | 120 |
| aaggttaggg | gtatgaacct | cacagttttt | ggtggtactg | ttacagcctt | ccttggtatt | 180 |
| ccttatgccc | aaccacctct | tggtagactt | aggttcaaga | agccacaaag | cctcaccaag | 240 |
| tggtctgaca | tttggaatgc | caccaagtat | gccaactcct | gttgtcaaaa | cattgaccaa | 300 |
| tccttcccag | gatttcatgg | atctgagatg | tggaacccaa | acactgacct | ctctgaggat | 360 |
| tgtctttacc | ttaatgtgtg | gatcccagcc | caaagccta | agaatgccac | tgttctcatt | 420 |
| tggatctatg | tggtggtttt | ccaaactgga | acctcctctc | tccatgttta | tgatggaaag | 480 |
| ttcttggcta | gagttgagag | agttattgtg | gtgagcatga | actatagggt | gggtgccttg | 540 |
| ggattcttgg | ccctcccagg | aaatcctgag | gccccaggta | atatgggtct | ttttgaccaa | 600 |
| caattggctc | ttcaatgggt | tcagaagaac | attgctgcct | ttggtggaaa | ccctaagtct | 660 |
| gttaccctct | tggagagtc | tgctggagct | gcttctgtta | gccttcactt | gctttctcct | 720 |
| ggaagccact | ccttgttcac | tagagccatt | ctccaatctg | gatccttcaa | tgctccttgg | 780 |
| gctgtgacat | ctctttatga | ggctaggaat | agaacattga | accttgctaa | gttgactggt | 840 |
| tgctctagag | agaatgagac | tgagatcatc | aagtgtctta | gaaacaagga | cccacaagag | 900 |
| attcttttga | atgaggcctt | tgttgttcct | tatggaaccc | ctttgtctgt | gaactttggt | 960 |
| cctacagtgg | atggtgattt | cctcactgac | atgccagaca | tcttgcttga | gcttggacaa | 1020 |
| ttcaagaaga | cccaaatttt | ggtgggtgtt | aacaaggatg | agggtacagc | tttccttgtg | 1080 |
| tatggcgcgc | tggttttag | caaggacaac | aactccatca | tcactagaaa | ggagttccaa | 1140 |
| gagggtctca | agatcttctt | cccaggagtg | tctgagtttg | gaaaggagtc | catccttttc | 1200 |
| cattacacag | attgggttga | tgaccaaaga | cctgagaact | atagggaggc | cttgggtgat | 1260 |
| gttgttggag | attacaactt | catttgccct | gccttggagt | tcaccaagaa | gttctctgag | 1320 |
| tggggaaata | atgccttctt | ctactacttt | gagcataggt | cctccaagct | cccttggcca | 1380 |
| gagtggatgg | gagtgatgca | tggttatgag | attgagtttg | ttttggttt | gcctcttgag | 1440 |
| agaagagata | actacacaaa | ggctgaggag | atcttgagca | gatccattgt | gaagaggtgg | 1500 |
| gccaactttg | ccaagtatgg | taatccaaat | gagactcaaa | acaatagcac | aagctggcct | 1560 |
| gtgttcaaga | gcactgagca | aaagtacctc | accttgaaca | cagagtccac | aaggattatg | 1620 |
| accaagttga | gggctcaaca | atgtaggttt | tggacatcct | tcttcccaaa | ggtgttggag | 1680 |
| atgacaggaa | atatcgatga | ggctgagtgg | gagtggaagg | ctggattcca | taggtggaac | 1740 |
| aactacatga | tggattggaa | gaaccaattc | aatgattaca | ctagcaagaa | ggagagctgt | 1800 |
| gtgggtctct | ctgagaagga | tgaactc | | | | 1827 |

<210> SEQ ID NO 2
<211> LENGTH: 1827
<212> TYPE: DNA
<213> ORGANISM: Artificial Sequence
<220> FEATURE:
<223> OTHER INFORMATION: Synthetic Primer

<400> SEQUENCE: 2

```
atgggacatt ctaaggttac tattatttgt attaggtttc ttttttggtt tcttcttctt      60
tgtatgctta ttggtaaatc tcatactgaa gatgatatta ttattgctac taagaatggt     120
aaggttagag gtatgaatct tactgttttt ggtggtactg ttactgcttt tcttggtatt     180
ccatatgctc aaccaccact tggtagactt aggttcaaga agccacaatc tcttactaag     240
tggtctgata tttggaatgc tactaagtat gctaattctt gttgtcaaaa cattgatcaa     300
tcttttccag ttttcatgg ttctgaaatg tggaatccaa atactgatct ttctgaagat     360
tgtctttatc ttaatgtttg gattccagct ccaaagccaa aaatgctac tgttcttatt     420
tggatatatg gtggtggttt tcaaactggt acttcttctc ttcatgttta tgatggtaaa     480
tttcttgcta gagttgaaag agttattgtt gtttctatga attacagagt tggtgctctt     540
ggttttcttg ctcttcctgg taatccagaa gctcctggta atatgggtct ttttgatcaa     600
caattggctc ttcaatgggt tcaaaaaaac atagctgctt tggtggtaa tccaaagtct     660
gttactcttt tggtgaatc tgctggtgct gcttctgttt ctcttcatct tctttctcct     720
ggttctcatt ctcttttac tagagctatt cttcaatctg gttcttttaa tgctccttgg     780
gctgttactt ctctttatga agctagaaat agaactctta atcttgctaa acttactggt     840
tgttctagag aaaatgagac tgagattatt aagtgtctta gaaacaaaga tccacaagaa     900
attcttctta atgaggcctt tgttgttcca tatggtactc cactttctgt taattttggt     960
ccaactgttg atggtgattt tcttactgat atgccagata ttcttcttga acttggtcaa    1020
ttcaagaaga ctcaaattct tgttggtgtt aacaaggatg aaggtactgc ttttcttgtt    1080
tatggcgcgc caggtttttc taaggataat aattctatta ttactagaaa ggaatttcaa    1140
gaaggtctta agatttttt tccaggtgtt tctgaatttg gtaaggaatc tattctttt     1200
cattatactg attgggttga tgatcaaaga ccagaaaatt acagagaagc tcttggtgat    1260
gttgttggtg attataattt tatttgtcct gctcttgagt ttactaagaa gttttctgaa    1320
tggggtaata atgcttttt ttattatttt gaacataggt cttctaaact tccttggcca    1380
gagtggatgg gtgttatgca tggttatgaa attgaattg ttttggtct tccacttgaa    1440
aggagagata ttacactaa ggctgaagaa attctttcta ggtctattgt taagagatgg    1500
gctaattttg ctaagtatgg taatccaaat gagactcaaa ataattctac ttcttggcct    1560
gtttttaagt ctactgaaca aaagtatctt actcttaata ctgaatctac taggattatg    1620
acaaaactta gggctcaaca atgtaggttt tggacttctt ttttccaaa ggttcttgaa    1680
atgactggaa acattgatga agctgaatgg gagtggaagg ctggttttca tagatggaat    1740
aattacatga tggattggaa gaatcaattc aatgattata cttctaagaa ggaatcttgt    1800
gttggtcttt ctgaaaagga tgaactt                                        1827
```

<210> SEQ ID NO 3
<211> LENGTH: 1827
<212> TYPE: DNA
<213> ORGANISM: Artificial Sequence
<220> FEATURE:
<223> OTHER INFORMATION: Synthetic Primer

<400> SEQUENCE: 3

```
atgggacaca gcaaggttac catcatttgc atcaggttcc tcttttggtt cctcctcctc    60
tgcatgctta ttggtaagag ccacactgag gatgacatca tcattgccac caagaatggt   120
aaggttaggg gtatgaacct cacagttttt ggtggtactg ttacagcctt ccttggtatt   180
ccttatgccc aaccacctct tggtagactt aggttcaaga agccacaaag cctcaccaag   240
tggtctgaca tttggaatgc caccaagtat gccaactcct gttgtcaaaa cattgaccaa   300
tccttcccag gatttcatgg atctgagatg tggaacccaa acactgacct ctctgaggat   360
tgtctttacc ttaatgtgtg gatcccagcc caaagccta agaatgccac tgttctcatt    420
tggatctatg gtggtggttt ccaaactgga acctcctctc tccatgttta tgatggaaag   480
ttcttggcta gagttgagag agttattgtg gtgagcatga actataggga gggtgccttg   540
ggattcttgg ccctcccagg aaatcctgag gccccaggta atatgggtct ttttgaccaa   600
caattggctc ttcaatgggt tcagaagaac attgctgcct ttggtggaaa ccctaagtct   660
gttaccctct ttggagagtc tgctggagct gcttctgtta gccttcactt gctttctcct   720
ggaagccact ccttgttcac tagagccatt ctccaatctg gatccttcaa tgctccttgg   780
gctgtgacat ctctttatga ggctaggaat agaacattga accttgctaa gttgactggt   840
tgctctagag agaatgagac tgagatcatc aagtgtctta gaaacaagga cccacaagag   900
attcttttga tgaggccttt gttgttcct tatggaaccc ctttgtctgt gaactttggt    960
cctacagtgg atggtgattt cctcactgac atgccagaca tcttgcttga gcttggacaa  1020
ttcaagaaga cccaaatttt ggtgggtgtt aacaaggatg agggtacatg gttccttgtg  1080
gctggcgcgc tggttttag caaggacaac aactccatca tcactagaaa ggagttccaa    1140
gagggtctca agatcttctt cccaggagtg tctgagtttg gaaaggagtc catccttttc  1200
cattacacag attgggttga tgaccaaaga cctgagaact ataggggaggc cttgggtgat  1260
gttgttggag attacaactt catttgccct gccttggagt tcaccaagaa gttctctgag  1320
tggggaaata atgccttctt ctactacttt gagcataggt cctccaagct cccttggcca  1380
gagtggatgg gagtgatgca tggttatgag attgagtttg ttttttggttt gcctcttgag  1440
agaagagata actacacaaa ggctgaggag atcttgagca gatccattgt gaagaggtgg  1500
gccaactttg ccaagtatgg taatccaaat gagactcaaa acaatagcac aagctggcct  1560
gtgttcaaga gcactgagca aaagtaccte accttgaaca cagagtccac aaggattatg   1620
accaagttga gggctcaaca atgtaggttt tggacatcct tcttcccaaa ggtgttggag   1680
atgacaggaa atatcgatga ggctgagtgg gagtggaagg ctggattcca taggtggaac   1740
aactacatga tggattggaa gaaccaattc aatgattaca ctagcaagaa ggagagctgt   1800
gtgggtctct ctgagaagga tgaactc                                       1827
```

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Ser Glu Lys Asp Glu Leu
1               5